US009165398B2

(12) United States Patent
Kim et al.

(10) Patent No.: US 9,165,398 B2
(45) Date of Patent: Oct. 20, 2015

(54) ANALYSIS OF FOOD ITEMS CAPTURED IN DIGITAL IMAGES

(75) Inventors: Kyungjin Kim, Seoul (KR); Kiwon Lee, Seongnam (KR); Sungil Cho, Seoul (KR); Jiyoung Hong, Seoul (KR); Sungeun Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 103 days.

(21) Appl. No.: 14/001,446

(22) PCT Filed: Feb. 25, 2011

(86) PCT No.: PCT/KR2011/001346
§ 371 (c)(1),
(2), (4) Date: Aug. 23, 2013

(87) PCT Pub. No.: WO2012/115297
PCT Pub. Date: Aug. 30, 2012

(65) Prior Publication Data
US 2013/0335418 A1    Dec. 19, 2013

(51) Int. Cl.
*G06F 19/00*  (2011.01)
*G06Q 10/00*  (2012.01)
*G06T 15/08*  (2011.01)

(52) U.S. Cl.
CPC .............. *G06T 15/08* (2013.01); *G06F 19/321* (2013.01); *G06F 19/3475* (2013.01); *G06Q 10/00* (2013.01)

(58) Field of Classification Search
CPC ........................... G06K 2209/17; A23L 1/293
See application file for complete search history.

(56) References Cited

U.S. PATENT DOCUMENTS

| 2002/0005855 | A1* | 1/2002 | Mehigan ...................... 345/596 |
| 2003/0076983 | A1 | 4/2003 | Cox |
| 2006/0074716 | A1* | 4/2006 | Tilles et al. ...................... 705/2 |
| 2006/0242164 | A1* | 10/2006 | Evans et al. .................... 707/100 |
| 2010/0111383 | A1 | 5/2010 | Boushey et al. |
| 2010/0173269 | A1 | 7/2010 | Puri et al. |
| 2011/0053121 | A1* | 3/2011 | Heaton ........................ 434/127 |

OTHER PUBLICATIONS

Zhu, Fengqing, et al. "The use of mobile devices in aiding dietary assessment and evaluation." Selected Topics in Signal Processing, IEEE Journal of 4.4 (2010): 756-766.*
Kim, SungYe, et al. "Development of a mobile user interface for image-based dietary assessment." Proceedings of the 9th International Conference on Mobile and Ubiquitous Multimedia. ACM, 2010.*

* cited by examiner

*Primary Examiner* — Zhengxi Liu
(74) *Attorney, Agent, or Firm* — Birch, Stewart, Kolasch & Birch, LLP

(57) ABSTRACT

Data analysis of a food item based on one or more digital images of the food item is disclosed. In one embodiment, the method comprises displaying, on a display unit of the smart device, first and second digital images of a meal, where the first digital image is captured before the second digital image. The method also comprises determining a volume of each food item in the first digital image and a volume of each food item in the second digital image by analyzing the first digital image and the second digital image using a digital image processing technique. The method further comprises generating, on the display unit, an amount of intake for the meal based on a difference between the volume of each food item in the first digital image and the volume of each food item in the second digital image.

14 Claims, 10 Drawing Sheets

ANALYSIS OF FOOD ITEMS CAPTURED IN DIGITAL IMAGES

TECHNICAL FIELD

Embodiments of the present disclosure relate to the field of electronics. More particularly, embodiments of the present disclosure relate to image processing.

BACKGROUND ART

Smart devices are devices that are digital, active, and computer networked. The smart devices are also user configurable and can operate to some extent autonomously. Some of the examples of the smart devices may include a personal computer (PC), a tablet PC, a smart TV, a mobile phone, a laptop computer, etc. Recently, the smart devices carry numerous features which enhance daily lives of those who use them.

DISCLOSURE OF INVENTION

Solution to Problem

One embodiment of the present disclosure pertains to a smart device for analyzing food items captured in a digital image, where the smart device comprises a display unit, a memory, and a processor coupled to the display unit and the memory. The processor is configured to display, on the display unit, a first digital image of a meal and a second digital image of the meal, where the first digital image of the meal is captured before the second digital image of the meal. The processor is also configured to determine a volume of each food item in the first digital image of the meal and a volume of each food item in the second digital image of the meal by analyzing the first digital image and the second digital image using a digital image processing technique. The processor is further configured to generate for displaying on the display unit an amount of intake for the meal based on a difference between the volume of each food item in the first digital image and the volume of each food item in the second digital image.

Another embodiment of the present disclosure pertains to a smart device for analyzing food items captured in a digital image, where the smart device comprises a display unit, a memory, a camera, and a processor coupled to the display unit, the memory, and the camera. The processor is configured to capture a first digital image of a food item using the camera and to display, on the display unit, the first digital image of the food item and metadata associated with the food item. The processor is also configured to perform an association of the food item on the first digital image with the metadata, and form a second digital image of the food item based on an input applied to the first digital image on the display unit. The processor is further configured to determine a volume of the food item in the first digital image and a volume of the food item in the second digital image using a digital image processing technique. Moreover, the processor is configured to generate for displaying on the display unit an amount of intake for the food item based on a difference between the volume of the food item in the first digital image and the volume of the food item in the second digital image as well as the metadata for the food item.

BRIEF DESCRIPTION OF DRAWINGS

Example embodiments are illustrated by way of example and not limitation in the figures of the accompanying drawings, in which like references indicate similar elements and in which.

Figure 1:
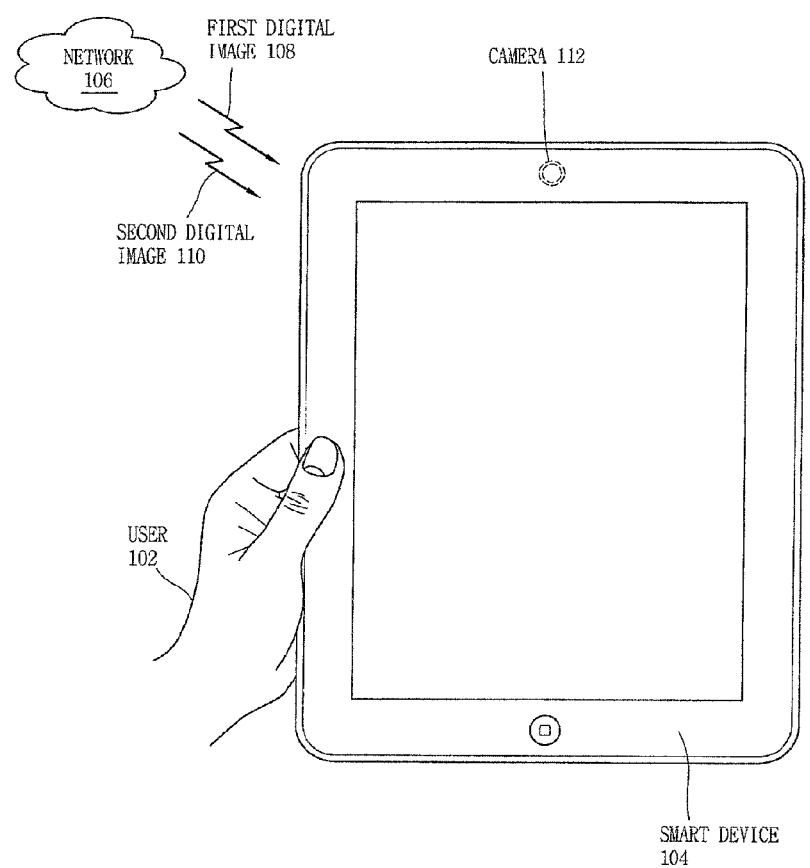
FIGS. 1-4 illustrate an exemplary view of a smart device for analyzing food items captured in two digital images, according to one embodiment of the present disclosure.

Other features of the present embodiments will be apparent from the accompanying drawings and from the detailed description that follows.

MODE FOR THE INVENTION

A smart device and method thereof that analyze food items captured in one or more digital images are disclosed. A user of a smart device may want to learn the amount of food consumed during a meal. Traditionally, the user may gather data or metadata (e.g., calorie information, nutrient weight information, etc.) for the food items included in the meal, and calculate the consumption by going over each food item and its associated information. The process in general is laborious and often takes time.

As a solution, the present disclosure provides a user interface, method and device which provide a quick and cost effective way of learning the amount of intake consumed by the user. In one embodiment, the amount of intake by the user for a meal is measured by digitally processing two captured images of the meal, where the volume of the meal consumed by the user is approximated based on the two digital images of the meal. One of the two images may be an image of the meal before it was eaten, and the other image may be an image of the meal after it was eaten. In addition, the two images may be loaded or received from an external device via a network. Alternatively, the two images may be captured using a camera of the smart device performing the analysis of the two digital images to obtain the amount of intake consumed by the user. Once the volumetric difference between the two digital images of the meal is obtained through processing the two images, the amount of intake for the meal consumed by the user is calculated based on the volumetric difference and metadata associated with each food item of the meal.

In another embodiment, the amount of food consumption may be approximated by digitally processing a single captured image of a food item which is about to be consumed by the user. In one example implementation of the embodiment, the digital image of a food item (or multiple food items) is displayed on the display unit of the smart device performing the image analysis of the digital image. In addition, metadata of the food item (e.g., calories per unit volume, nutrient weight per unit volume, etc.) is associated with the food item. Further, the user, using a finger or stylus, may identify a portion of the food item the user intends to consume. When the user marks the portion on the digital image of the food item, the volumetric measurement of the portion is measured through digitally processing the image of the meal. Then, the amount of intake for the portion of the food item is calculated based on the volume of the portion and the metadata associated with the food item.

In yet another embodiment, a recommended amount of intake for particular food item(s) may be suggested for the user. In one example implementation of the embodiment, the user may sign up for a diet watch program. For unit duration of the diet watch, such as from noon (before lunch) to 5 p.m. (before dinner), the user may capture a digital image of any food the user consumes. Using a similar digital image processing technique discussed in the other two embodiments, the amount of intake consumed by the user (e.g., lunch, snack, etc.) may be accumulated. Further, whenever the user captures an image of a food item the user is about to eat, a recommended portion of the food item may be displayed on the display unit of the smart device. The recommend amount of intake (e.g., in calories) may be calculated by subtracting the accumulated amount of intake from the threshold value assigned for the duration (e.g., the total calories the user is allowed to consume for the duration). Then, the amount of amount of intake is translated into the recommended portion of the food item by multiplying the amount of intake in calorie with volume per unit calorie associated with the food item. Further, the recommend portion of the food item is generated based on the volumetric data which correspond to the recommended portion of the food item, and is displayed on the display unit of the smart device.

As described above, the present disclosure provides a smart device and method thereof for analyzing one or more images of food item(s). More particularly, the smart device according to the present disclosure provides a user-friendly user interface which makes it convenient for the user to be aware of each food item the user has consumed or is about to consume.

Reference will now be made in detail to the embodiments of the disclosure, examples of which are illustrated in the accompanying drawings. While the disclosure will be described in conjunction with the embodiments, it will be understood that they are not intended to limit the disclosure to these embodiments. On the contrary, the disclosure is intended to cover alternatives, modifications and equivalents, which may be included within the spirit and scope of the disclosure. Furthermore, in the detailed description, numerous specific details are set forth in order to provide a thorough understanding of the present disclosure. However, it will be obvious to one of ordinary skill in the art that the present disclosure may be practiced without these specific details. In other instances, well known methods, procedures, components, and circuits have not been described in detail as not to unnecessarily obscure aspects of the present disclosure.

FIGS. 1-4 illustrate an exemplary view of a smart device 104 for analyzing food items captured in two digital images, according to one embodiment of the present disclosure. In FIG. 1, a user 102 is operating the smart device 104 connected to a network 106. In one embodiment, the smart device 104 is equipped with a camera 112. Further, FIG. 1 illustrates the smart device 104 receiving from the network 106 a first digital image 108 (e.g., an image of a meal before it is eaten) and a second digital image 110 (e.g., an image of the meal after it is eaten). It is appreciated that the smart device 104 may be any one of a personal computer (PC), a tablet PC, a smart TV, a mobile phone, a laptop computer, etc. It is further appreciated that the network 106 may be any combination of a short range network, a local area network (LAN), a home area network, a campus network, a global area network, an enterprise private network, a virtual private network, an internetwork, an Internet, an intranet and extranet, an overlay network, etc.

In one embodiment, as illustrated in FIG. 1, the first digital image 108 and the second digital image 110 are received by a transceiver, although not shown, of the smart device 104. In an alternative embodiment, the camera 112 may be used to capture the first digital image 108 and the second digital image 110. In one example embodiment, the camera 112 may be an analog or digital device, which generates a digital image that can be captured in visible or non-visible spectrum, such as infrared or any other radiated illumination that produces an image containing discernable object(s).

Figure 2:
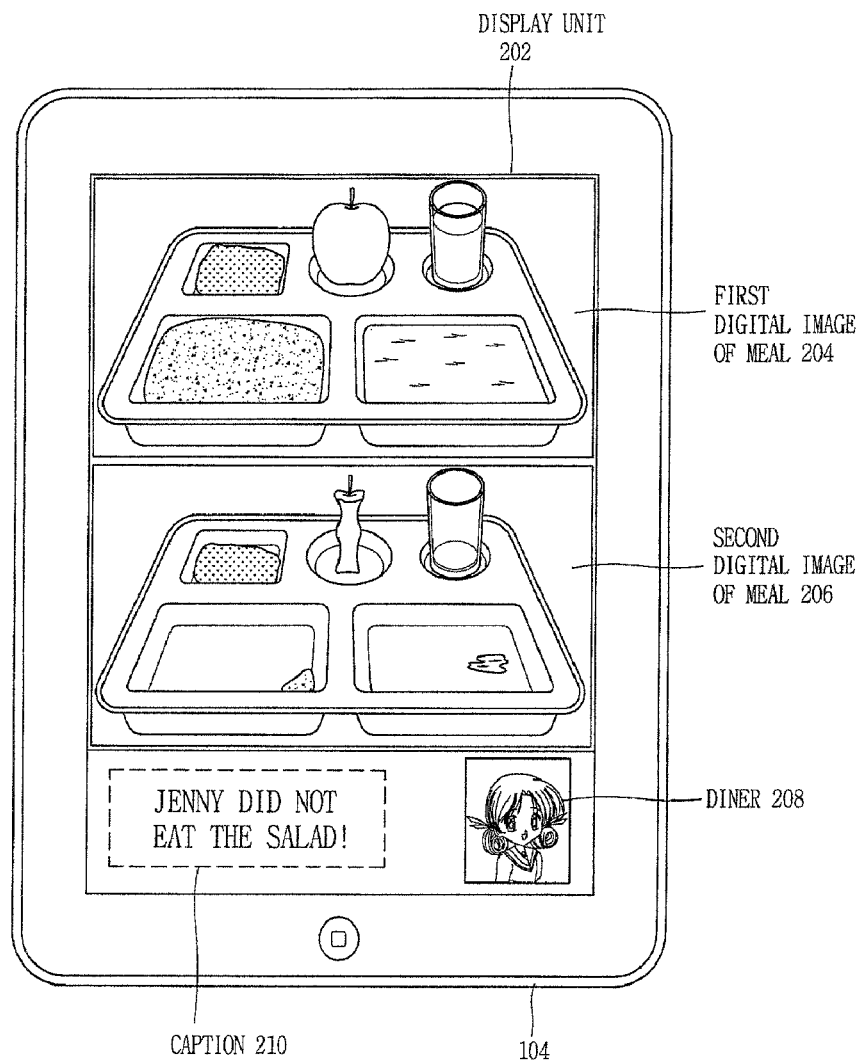

FIG. 2 illustrates an exemplary view of the smart device 104 in FIG. 1 displaying the first digital image 108 and the second digital image 110 on a display unit 202 of the smart device 104. In one example embodiment, the first digital image 108 is a first digital image of meal 204, which may be a meal before it is eaten, and the second digital image 110 is a second digital image of meal 206, which may be the meal after it is eaten. As illustrated in FIG. 2, the meal on the first digital image of meal 204 and/or the second digital image of meal 206 may include one or more food items (e.g., rice, soup, salad, apple, beverage, etc.). Further, the example view of the smart device 104 may include an image of a diner 208 who has consumed the meal on the first digital image 204 and/or the second digital image 206. Further, the example view may include a caption 210 which lists notable things from the first digital image of meal 204 and the second digital image of meal 206, such as the diner 208 (e.g., Jenny) not eating the salad in the meal.

Figure 3:
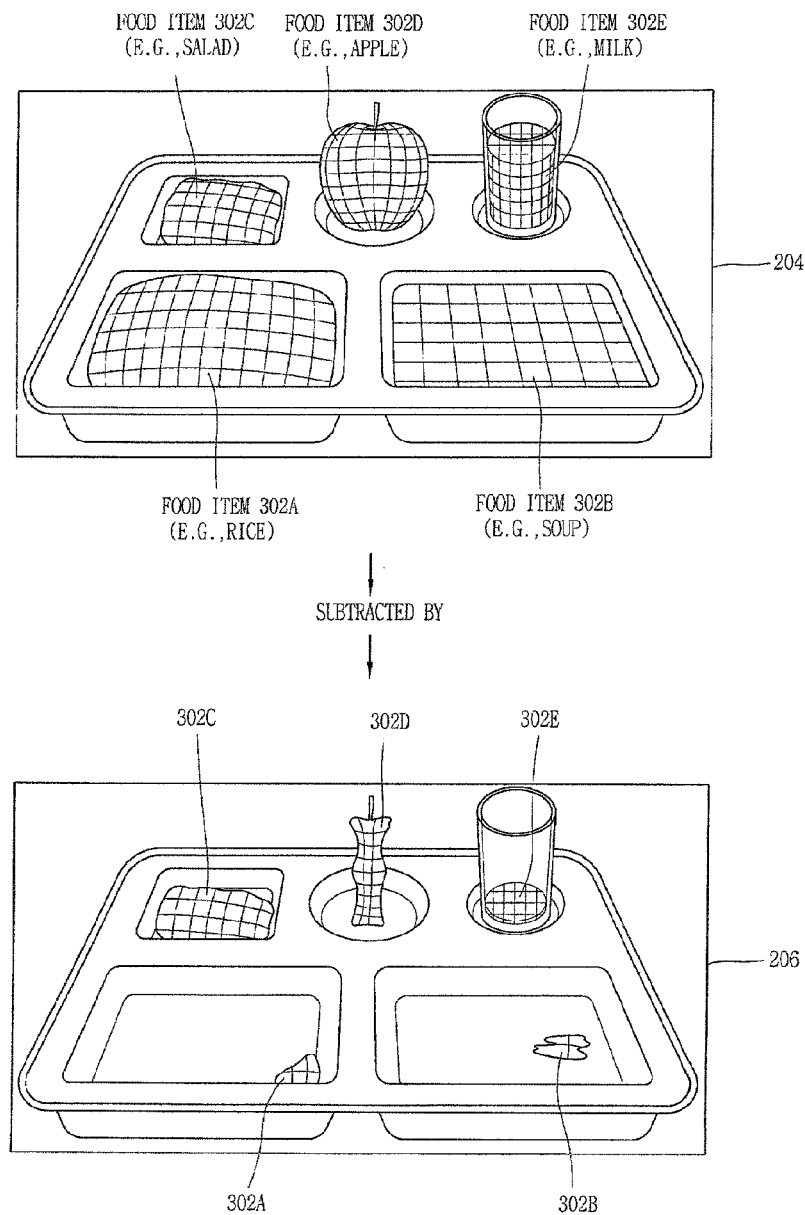

FIG. 3 illustrates an exemplary view of the smart device 104 of FIG. 1 analyzing the first digital image of meal 204 and the second digital image of meal 206 using a digital image processing technique or algorithm. It is appreciated that digital image processing is any form of signal processing for which the input is an image, such as a photograph or video frame, and the output may be either an image or, a set of characteristics or parameters related to the image. For example, using the digital image processing technique or algorithm, the first digital image of meal 204 and the second digital image of meal 206 are converted into a set or organized pixels in any digital format including but not limited to JPEG, PNG, bitmap, etc.

Through using the digital image processing technique or algorithm and one or more reference values (e.g., such as the size of the unit pixel in the first digital image of meal 204 and the second digital image of meal 206, the size of an object in X-Y plane and how the size translates to a volume of the object in 3-D plane, etc.), a volume of each food item in the first digital image of meal 204 and a volume of each food item in the second digital image of meal 206 are determined. For example, by digitally analyzing the first digital image of meal 204, i.e., the meal before it is eaten, the volume of food item 302A (e.g., rice), the volume of food item 302B (e.g., soup), the volume of food item 302C (e.g., salad), the volume of food item 302D (e.g., apple), and the volume of food item 302E (e.g., milk) are obtained. In addition, by digitally analyzing the second digital image of meal 206, i.e., the meal after it is eaten, the volume of food item 302A (e.g., rice), the volume of food item 302B (e.g., soup), the volume of food item 302C (e.g., salad), the volume of food item 302D (e.g., apple), and the volume of food item 302E (e.g., milk) are obtained. Further, by subtracting the volume of each food item before it is eaten by the volume of the corresponding food item after it is eaten, the consumed volume of each food item is obtained. Thus, the volume of food item 302A (e.g., rice) consumed can be obtained by subtracting the volume of food item 302A in the second digital image 206 from the volume of food item 302A in the first digital image of meal 204.

Figure 4:
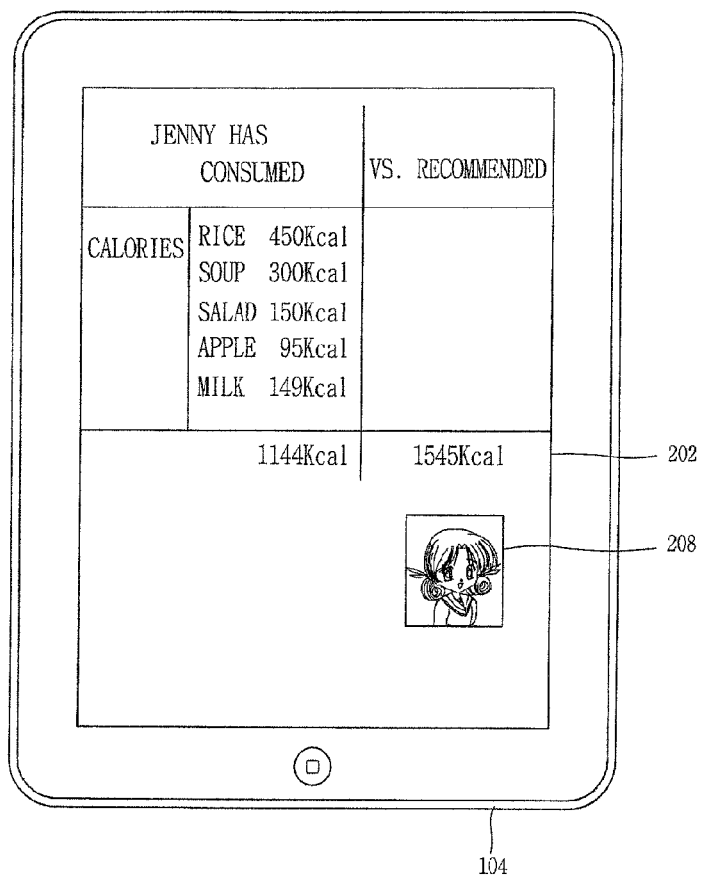

FIG. 4 illustrates an exemplary view of the smart device 104 in FIG. 1 displaying an amount of intake consumed by the diner 208 on the display unit 202. In FIG. 4, the amount of intake is in calories, where the diner 208 (e.g., Jenny) has consumed 450 Kcal of rice, 300 Kcal of soup, 150 Kcal of salad, 95 Kcal of apple, and 149 Kcal of milk. In one example embodiment, the amount of intake for each food item (e.g., rice) in calories may be obtained by first calculating a difference between the volume of each food item in the first digital image of meal 204 (e.g., 3.5 in3) and the second digital image of meal 206 (e.g., 0.5 in3). Then, the difference in volume of each food item (e.g., 3 in3) is multiplied by calories per unit volume of each food item (e.g., 150 Kcal/in3).

In an alternative embodiment, the amount of intake may be represented in terms of nutrient weight. Further, the recommended calorie intake (e.g., 1545 Kcal) for the diner 208 is also listed so that the diner 208 can make an informed decision about her eating.

Figure 5:
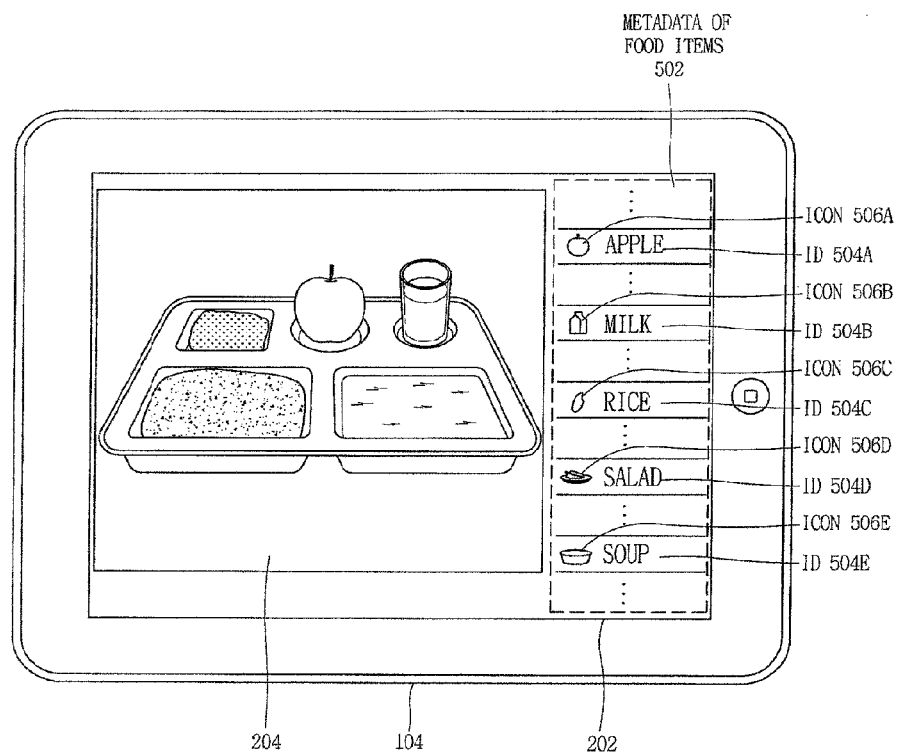
FIGS. 5-8 illustrate exemplary user interface views of the smart device in FIGS. 1-4, according to one embodiment of the present disclosure.

FIGS. 5-8 illustrate exemplary user interface views of the smart device 104 in FIGS. 1-4, according to one embodiment of the present disclosure. FIG. 5 illustrates an example user interface view of the smart device 104 displaying the first digital image of meal 204, which may be an image of the meal before it is eaten, and metadata of food items 502. In one embodiment, the metadata of food items 502 may be a list of food items and information about each food item (e.g., calorie data, nutrient data, etc.). Accordingly, the user 102 may scroll up and/or down to locate the food items relevant to the first digital image of meal 204.

In an alternative embodiment, the metadata of food items 502 may identify only the food items shown on the first digital image of meal 204 and display information associated with the food items (e.g., an icon for each food item, an identifier (ID) for each food item, etc.) in the first digital image of meal 204. Further, although it is not shown, more information, such as calorie for each unit of food item and/or nutrient weight for each unit of food item, may be included as the metadata of food items 502. For example, as illustrated in FIG. 5, the identifiers of the food items on the first digital image of meal 204 are displayed as ID 504A-E, and the icons of the food items are displayed as icon 506A-E.

Figure 6:
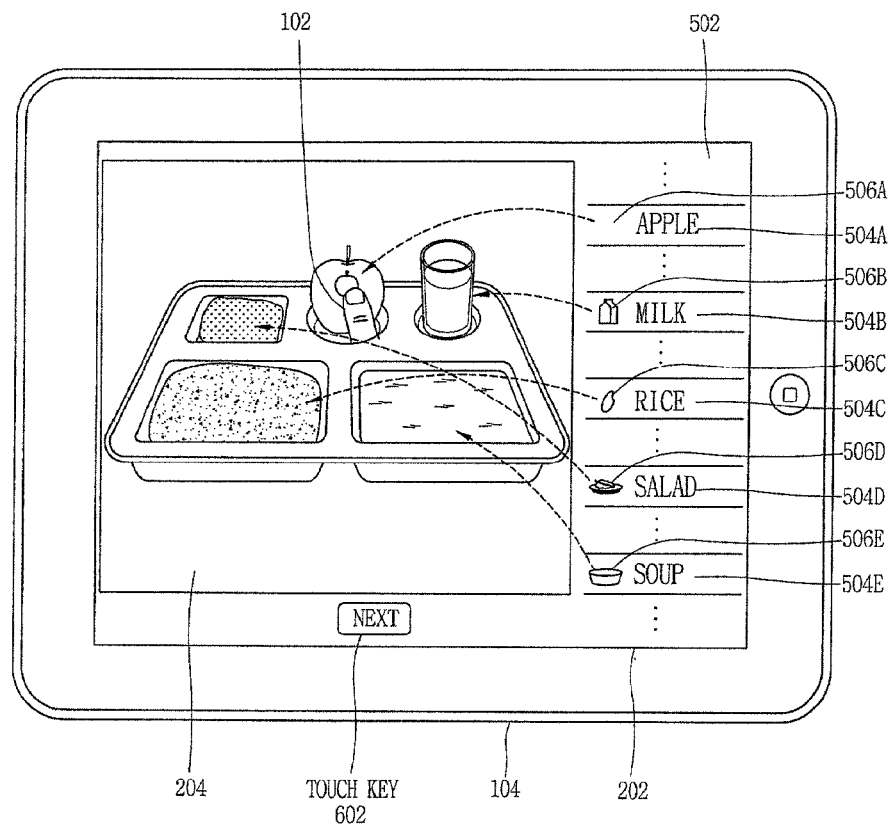

FIG. 6 illustrates an example user interface view of associating the metadata of food items 502 to corresponding food items on the first digital image of meal 204. In one embodiment, each food item on the first digital image of meal 204 is associated with a respective item of the metadata 502. In one example implementation, each food item is associated with the respective item of the metadata 502 when the respective item of the metadata 502 is moved (e.g., dragged) within a domain of each food item displayed on the display unit 202.

For example, the user 102 may use a finger tip to move (e.g., drag) an icon of a corresponding metadata item from the list of metadata of food items 502 to an image of the corresponding food item in the first digital image of meal 204. In FIG. 6, the icon for 'apple' 506A is placed on the image of apple on the first digital image of meal 204, and the metadata for 'apple' is applied. Accordingly, icons for the remaining food items may be dragged onto their corresponding destinations on the first digital image of meal 204. In an alternative embodiment, the metadata for each food item on the first digital image of meal 204 is automatically applied without any intervention from the user 102. Then, the user 102 may press a touch key 602 labeled 'next' to move onto next step.

Figure 7:
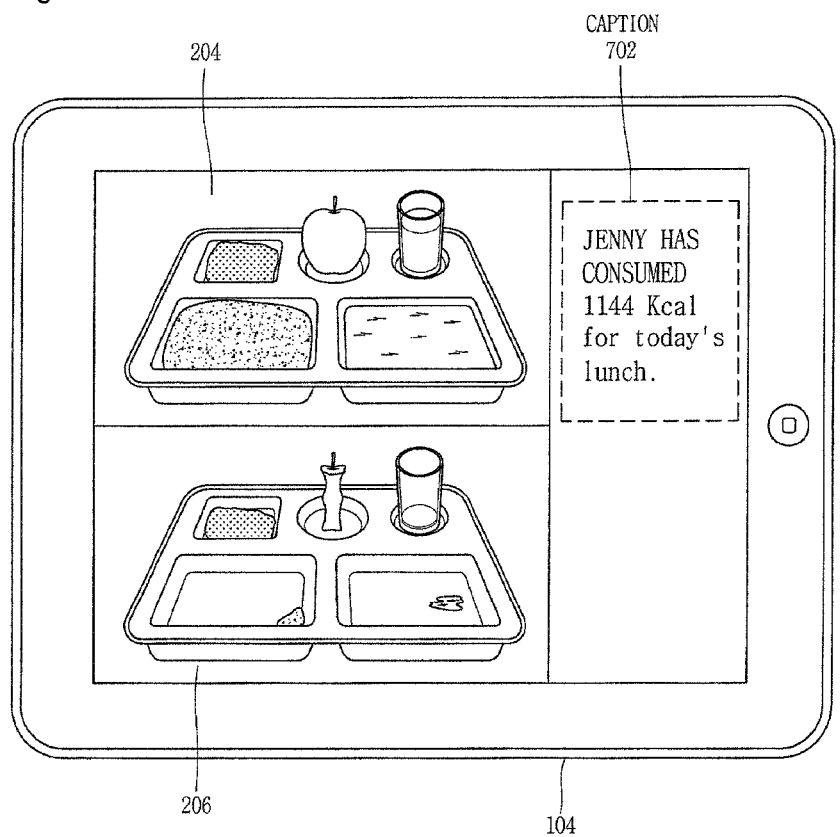

FIG. 7 illustrates an example user interface view of the smart device 104 in FIG. 1 displaying the amount of intake. Once the metadata for each food item on the first digital image of meal 204 are identified and applied as described in FIGS. 5 and 6, through analyzing the first digital image of meal 204 and the second digital image of meal 206 using a digital image processing technique or algorithm as described in FIG. 3, the amount of intake for the meal is calculated. FIG. 7 illustrates an example view of the smart device displaying the first digital image of meal 204 and the second digital image of meal 206 and a caption 702 informing the amount of intake obtained by analyzing the first digital image of meal 204 and the second digital image of meal 206.

Figure 8:
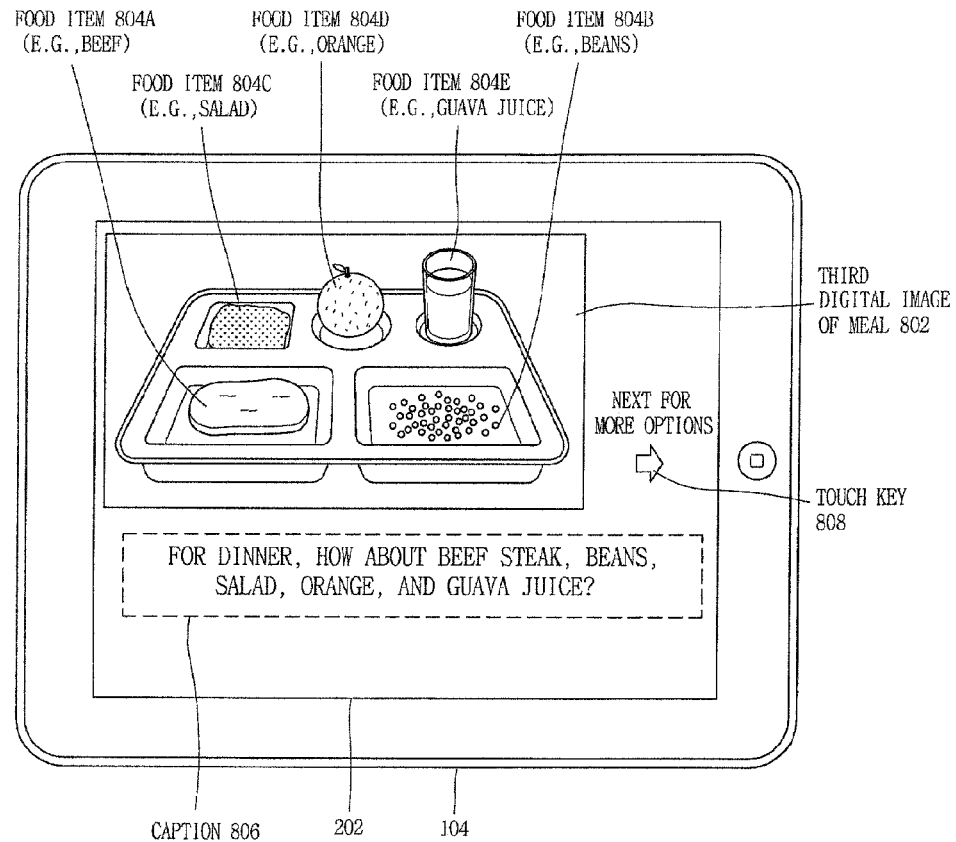

FIG. 8 illustrates an example user interface view of the smart device 104 in FIG. 1 displaying an image of a recommended meal. In FIG. 8, a third digital image of meal 802 is displayed on the display unit 202 of the smart device 104, where the third digital image of meal 802 is a recommended meal based on the analysis of the first digital image of meal 204 and the second digital image of meal 206 (e.g., the amount of intake of the meal), the recommended amount of calorie intake for the meal as illustrated in FIG. 4, the total daily amount of food intake recommended for the user 102 (e.g., or the diner 208), etc.

For example, the recommended amount of intake (e.g., in calories, in nutrient weight, etc.) for next meal may be calculated based on data such as the amount of intake of the food items from the first and second digital images of a meal, the amount of intake for other food consumed by the user 102 (e.g., or the diner 208), the total daily amount of food intake recommended for the user 102 (e.g., or the diner 208), etc. Once the recommended amount of intake for next meal is determined, one or more candidate images of next meal are generated, where each food item in the next meal is selected based on the recommended amount of intake for next meal and/or the known food preference by the user 102. In FIG. 8, beef, beans, salad, orange, and guava juice are selected as food items 804A-E recommended for next meal. In addition, a caption 806 is displayed with a suggestion for the recommended meal for the user 102. The user 102 may press a touch key 808 for more options.

Figure 9:
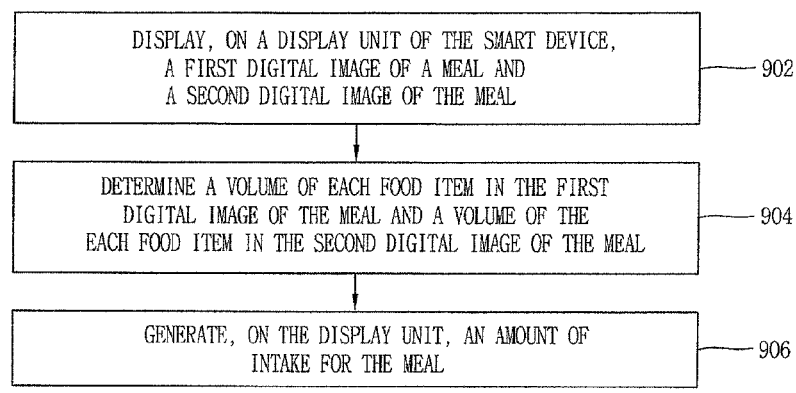
FIG. 9 illustrates a process flow chart of an exemplary method of the smart device in FIGS. 1-8 for analyzing food items captured in two digital images, according to one embodiment of the present disclosure.

FIG. 9 illustrates a process flow chart of an exemplary method of the smart device in FIGS. 1-8 for analyzing food items captured in two digital images, according to one embodiment of the present disclosure. In keeping with the previous examples, particular components described with respect to FIGS. 1-8 are referenced as performing the process in FIG. 9. It should be noted that the components that are referred to as performing the process are for illustrative purposes only. In some implementations, other components, or a different combination of components within a system, may instead perform the process in FIG. 9.

In operation 902, as illustrated in FIGS. 1 and 2, the first digital image of meal 204 and the second digital image of meal 206 are displayed on the display unit 202 of the smart device 104, where the first digital image of meal 204 is captured before the second digital image of meal 206. In one embodiment, the first digital image of meal 204 and the second digital image of meal 206 are received from an external device. In one embodiment, the first digital image of meal 204 and the second digital image of meal 206 are captured using the camera 112 implemented on the smart device 104.

In one embodiment, as illustrated in FIG. 5, the metadata 502 of each food item in the first digital image of meal 204 in FIG. 2 is displayed on the display unit 202 of the smart device 104. The metadata 502 may comprise identification data of each food item (504A-E). The metadata 502 may further comprise an icon for each food item (e.g., 506A-E). In one embodiment, as illustrated in FIG. 6, each food item on the first digital image of meal 204 may be associated with a respective item of the metadata 502, for example, by dragging a respective item of the metadata 502 to a domain of each food item displayed on the display unit 202.

In operation 904, as illustrated in FIG. 3, the volume of each food item in the first digital image of meal 204 and the volume of each food item in the second digital image of meal 206 are determined by analyzing the first digital image of meal 204 and the second digital image of meal 206 using a digital image processing technique. In operation 906, as illustrated in FIG. 4, the amount of intake for the meal is generated based on the difference between the volume of each food item in the first digital image of meal 204 and the volume of each food item in the second digital image of meal 206. Further, as illustrated in FIG. 8, an image of one or more food items may be recommended for next meal.

It is appreciated that the methods disclosed in FIG. 9 may be implemented in a form of a machine-readable medium embodying a set of instructions that, when executed by a machine, cause the machine to perform any of the operations disclosed herein.

Figure 10:
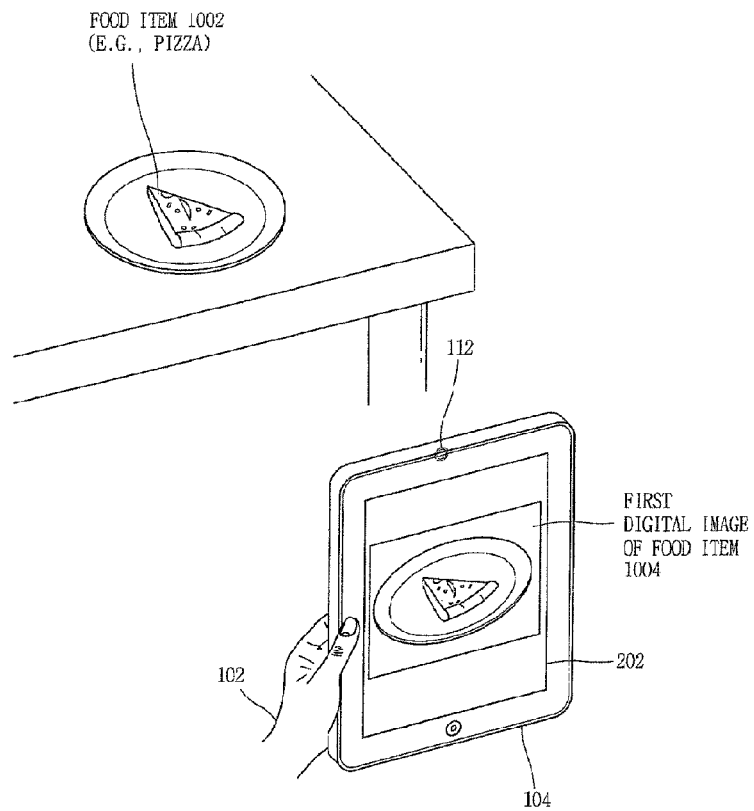
FIGS. 10-13 illustrate an exemplary view of a smart device for analyzing food items captured in a digital image, according to one embodiment of the present disclosure.

FIGS. 10-13 illustrate an exemplary view of the smart device 104 for analyzing food items captured in a digital image, according to one embodiment of the present disclosure. More particularly, FIG. 10 illustrates an example view of the smart device 104 capturing a first digital image of a food item 1004 using the camera 112. The camera 112 may be a digital camera or an analog camera with a system to convert the image captured into a digital image. Further, the camera 112 may be a two-dimensional or three-dimensional camera. Further yet, the camera 112 may capture still images and/or moving images.

In one example embodiment, as illustrated in FIG. 10, the user 102 may take a picture of a food item 1002 (e.g., pizza) using the smart device 104. Then, the smart device 104 may display the first digital image of food item 1004 on the display unit 202 of the smart device 104. It is appreciated that more than two food items may be captured for analysis, although FIG. 10 illustrates an example with a single food item.

Figure 11:
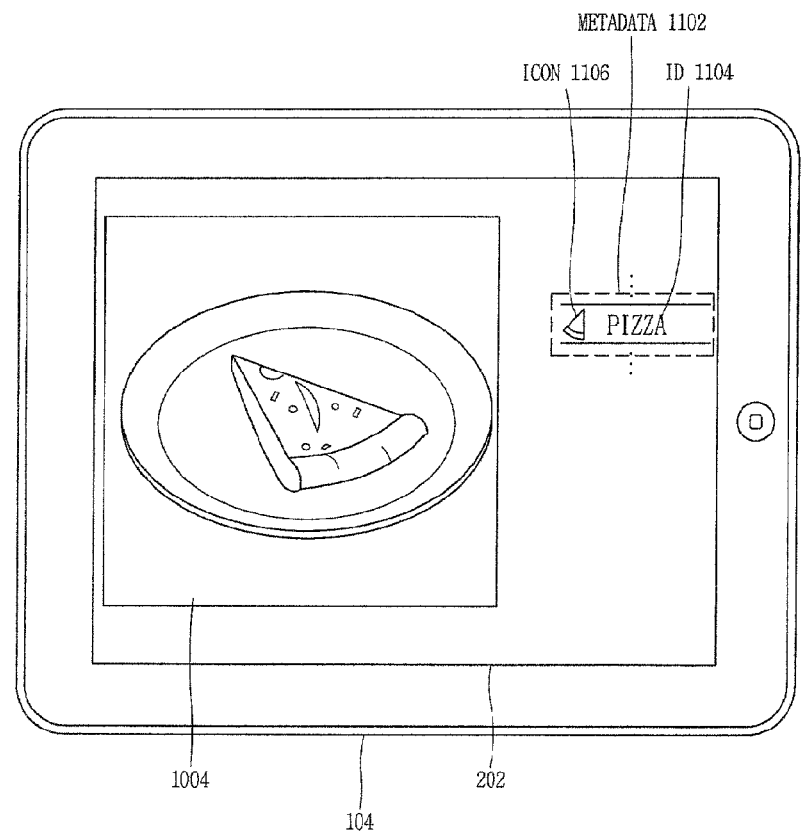

FIG. 11 illustrates an example view of the display unit 202 of the smart device 104 displaying the first digital image of food item 1004 and metadata 1102 associated with the food item 1002. In one embodiment, as illustrated in FIG. 11, only the metadata 1102 (e.g., an ID 1104 and an icon 1106) which corresponds to the first digital image of food item 1004 may be displayed on the display unit 202 of the smart device 104. Alternatively, a list of metadata may be displayed on the display unit, and the user 102 may scroll up and/or down to locate the metadata 1102 which corresponds to the first digital image of food item 1004.

Figure 12:
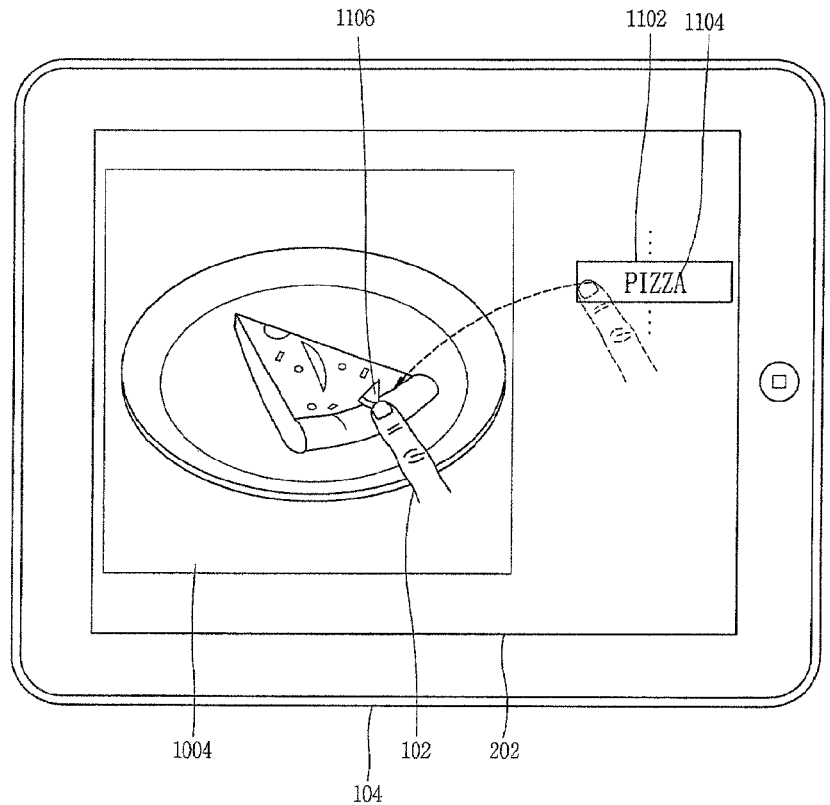

FIG. 12 illustrates an exemplary view of the display unit 202 of the smart device 104 displaying the metadata 1102 being associated with the digital image of food item 1004. In one embodiment, the association of the metadata 1102 with the first digital image of food item 1004 may be performed when the metadata 1102 is moved (e.g., dragged) within a domain of the first digital image of food item 1004 displayed on the display unit 202 of the smart device 104. In one example implementation, as illustrated in FIG. 12, the metadata 1102 is associated with the first digital image of food item 1004 when the icon 1106 is dragged away from the metadata 1102 and placed on the first digital image of food item 1004 using a finger or stylus of the user 102.

Figure 13:
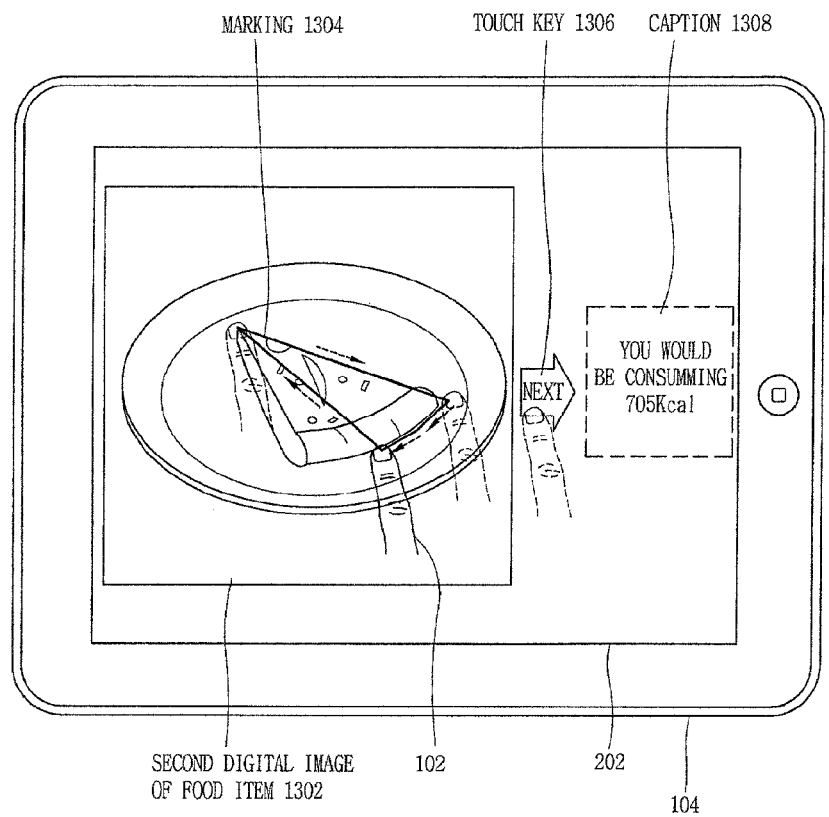

FIG. 13 illustrates an example view of the display unit 202 of the smart device 104 displaying the user 102 performing a marking 1304 identifying a portion of the first digital image of food item 1004 to generate a second digital image of food item 1302. In one embodiment, the second digital image of food item 1302 is generated based on an input applied to the first digital image of food item 1004 displayed on the display unit. 202. In one example implementation, the user 102 may use a finger or stylus to designate a portion the user 102 intends to consume. In FIG. 13, the user 102 uses a finger to draw a triangular shape on the first digital image of food item 1004 (e.g., pizza) to generate the second digital image of food item 1302 with the marking 1304.

When the user 102 presses a touch key 1306 (e.g., a 'next' button) which initiates an image analysis for the second digital image of food item 1302, the digital image analysis for the second digital image of food item 1302 is performed based on the metadata 1102. It is appreciated that the digital image analysis of the second digital image of food item 1302 may be similar to the one described in FIG. 3.

In one embodiment, the digital image analysis for the second digital image of food item 1302 may include a step for multiplying the size measuring the portion of the food item selected or marked by the user 102 with a unit calorie or unit nutrient weight to generate the amount of intake the user 102 would have consumed had the user 102 eaten the portion designated on the second digital image of food item 1302. More particularly, the digital image analysis would include a step for calculating the size (e.g., volume) measuring the portion of the food item designated by the user 102. Once the digital image analysis for the second digital image of food item 1302 is completed, a caption 1308 is generated to display the amount of intake which would be consumed by eating the portion.

In an alternative embodiment, the digital image analysis may include a step for generating on the display unit 202 an amount of intake for the portion of the food item (e.g., pizza) based on a difference between the volume of the food item in the first digital image of food item 1004 and the volume of the food item in the second digital image of food item 1302 and the metadata 1102, where the second digital image of food item 1302 in this case would not show the portion designated to be eaten by the user (e.g., the triangular shape drawn by the user 102). Accordingly, the difference between the volume of the food item in the first digital image of food item 1004 and the volume of the food item in the second digital image of food item 1302 would amount to the portion designated to be eaten by the user 102. The difference in volume may be multiplied by calorie(s) per unit volume of the food item or nutrient weight(s) per unit volume to generate the amount of intake the user 102 would have consumed had the user 102 eaten the portion designated on the second digital image of food item 1302.

Figure 14:
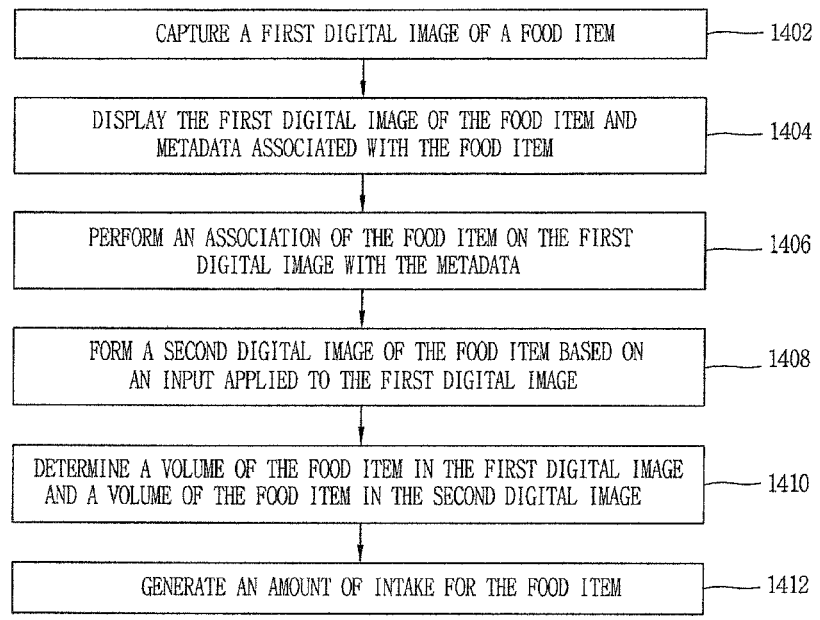
FIG. 14 illustrates a process flow chart of an exemplary method of the smart device in FIGS. 10-13 for analyzing food items captured in a digital image, according to one embodiment of the present disclosure.

FIG. 14 illustrates a process flow chart of an exemplary method of the smart device 104 in FIGS. 10-13 for analyzing food items captured in a digital image, according to one embodiment of the present disclosure. In keeping with the previous examples, particular components described with respect to FIGS. 10-13 are referenced as performing the process in FIG. 14. It should be noted that the components that are referred to as performing the process are for illustrative purposes only. In some implementations, other components, or a different combination of components within a system, may instead perform the process in FIG. 14.

In operation 1402, as illustrated in FIG. 10, the first digital image of food item 1004 is captured using the camera 112. In operation 1404, as illustrated in FIG. 11, the first digital image of food item 1004 and the metadata 1102 associated with the food item are displayed on the display unit 202. In one embodiment, the metadata 1102 comprises calories per unit volume for the food item. In operation 1406, as illustrated in FIG. 12, an association of the food item on the first digital image of food item 1004 with the metadata 1102 is performed. In one embodiment, the association of each food item to the metadata 1102 is performed when the metadata 1102 is moved within a domain of the food item displayed on the display unit. 202. In operation 1408, as illustrated in FIG. 13, the second digital image of food item 1302 is generated based on an input applied to the first digital image of food item 1004 on the display unit 202. In one embodiment, the input applied to first digital image of food item 1004 comprises designation of a portion of the food item using the marking 1304 on the food item present on the first digital image of food item 1. In one example implementation, the marking on the food item is performed using a finger or a stylus.

In operation 1410, in a manner similar to the digital image processing technique described in FIG. 3, the volume of the food item in the first digital image of food item 1004 and the volume of the food item in the second digital image of food item 1302 are determined using a digital image processing technique. In operation 1412, as illustrated in FIG. 13, the amount of intake for the food item is generated based on a difference between the volume of the food item in the first digital image of food item 1004 and the volume of the food item in the second digital image of food item 1302 and the metadata 1102 for the food item. In one embodiment, the amount of intake is obtained by multiplying the calories per unit volume for the food item and the difference between the volume of the food item in the first digital image of food item 1004 and the volume of the food item in the second digital image of food item 1302.

It is appreciated that the methods disclosed in FIG. 14 may be implemented in a form of a machine-readable medium embodying a set of instructions that, when executed by a machine, cause the machine to perform any of the operations disclosed herein.

Figure 15:
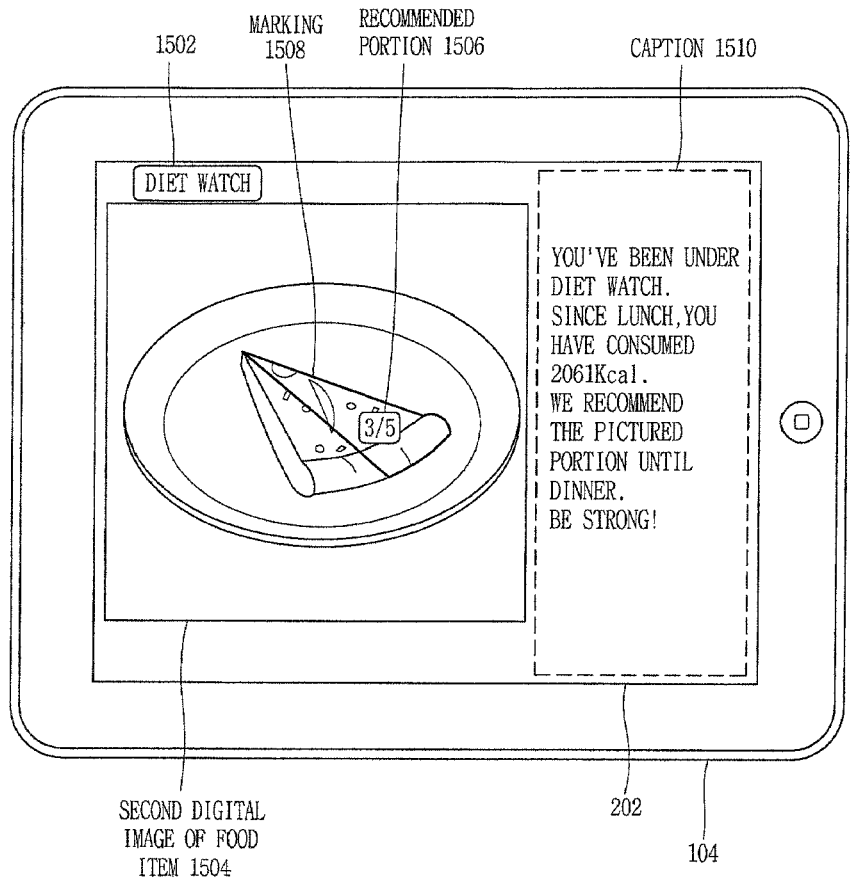
FIG. 15 illustrate another exemplary view of the smart device in FIGS. 10-13 for analyzing food items captured in a digital image, according to one embodiment of the present disclosure.

FIG. 15 illustrates another exemplary view of the smart device 104 in FIGS. 10-13 for analyzing food items captured in a digital image, according to one embodiment of the present disclosure. In FIG. 15, a recommended portion 1506 of the food item (e.g., three-fifths of the food item captured on the first digital image of food item 1004) with a marking 1508 is displayed on the display unit 202. The provision of the recommended portion 1506 may be a part of a diet program the user 102 subscribes to. For example, if the user 102 is registered with a diet program called 'diet watch' 1502, the user 102 may capture digital images of food items the user 102 consumes for the period the user 102 is under the diet watch 1502.

For example, the diet watch 1502 may last from noon (e.g., before lunch) to 5 p.m. (e.g., before dinner) of the same day. Then, as the user 102 consumes a sandwich for lunch, the user 102 may take a picture of the sandwich using the camera 112 of the smart device 104. Upon taking the picture, the amount of intake in calorie may be calculated by analyzing the digital image of the sandwich. After lunch, if the user 102 wants to each some snack (e.g., a piece of pizza), the user 102 may take a picture of the pizza piece and run a menu of the diet watch 1502 which displays a recommended portion of the pizza. When the picture of the pizza is taken, the cumulated amount of intake (e.g., the calorie amount for the sandwich consumed during lunch, such as 1205 Kcal) may be subtracted from the allowed calories for the period under the diet watch 1502 (e.g., 1551 Kcal) to calculate the remaining calorie amount which can be consumed by the user 102 during the period under the diet watch 1502. Then, the remaining calorie amount (e.g., 346 Kcal) is compared to the total calorie amount of the pizza piece provided that the piece is eaten by the user 102 in entirety (e.g., 580 Kcal). Based on the comparison, the portion of the pie (e.g., three-fifths) which corresponds to or less than the remaining calorie amount is proposed to the user 102 as illustrated in a second digital image of food item 1504. Further, the caption 1510 may be displayed on the display unit 202 along with the pizza piece and the marking 1508 to identify the recommended portion.

Figure 16:
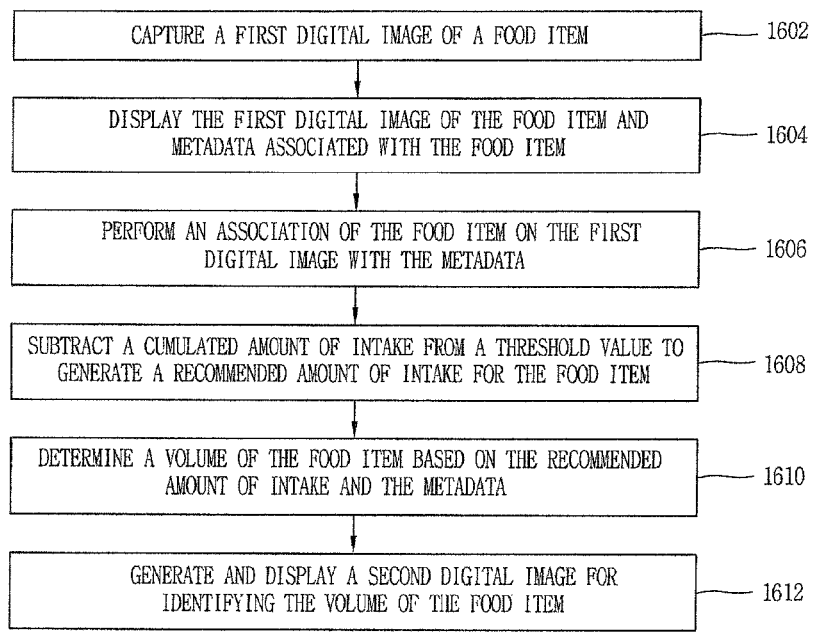
FIG. 16 illustrates a process flow chart of an exemplary method of the smart device in FIG. 15 for analyzing food items captured in a digital image, according to one embodiment of the present disclosure.

FIG. 16 illustrates a process flow chart of an exemplary method of the smart device 104 in FIG. 15 for analyzing food items captured in a digital image, according to one embodiment of the present disclosure. In keeping with the previous examples, particular components described with respect to FIGS. 10-12 and 15 are referenced as performing the process in FIG. 16. It should be noted that the components that are referred to as performing the process are for illustrative purposes only. In some implementations, other components, or a different combination of components within a system, may instead perform the process in FIG. 16.

In operation 1602, as illustrated in FIG. 10, the first digital image of food item 1004 is captured using the camera 112. In operation 1604, as illustrated in FIG. 11, the first digital image of food item 1004 and the metadata 1102 associated with the food item are displayed on the display unit 202. In one embodiment, the metadata 1102 comprises calories per unit volume for the food item. In operation 1606, as illustrated in FIG. 12, an association of the food item on the first digital image of food item 1004 with the metadata 1102 is performed. In one embodiment, the association of the food item with the metadata 1102 is performed when the metadata 1102 is moved within a domain of the food item displayed on the display unit 202. In operation 1608, a cumulated amount of intake, for example, the calorie amount of the food consumed by the user 102 or the diner 208 during a certain period of a day under the diet watch 1502 such as from noon (before lunch) to 5 pm (before dinner), is subtracted from a threshold value set as the recommended amount of intake for the certain period of the day set by the diet watch 1502 in order to generate a recommended amount of intake for the food item.

In operation 1610, the volume of the food item presented on the first digital image of food item 1004 which amounts to the recommended amount of intake is determined based on the recommended amount of intake and the metadata 1102. In one embodiment, the recommended amount of intake (e.g., in calories) is multiplied by the metadata 1102 in volume per unit calorie to generate the volume for the recommended amount of intake for the food item. In operation 1612, the second digital image 1504 for identifying the (recommended) volume or portion of the food item is generated and displayed on the display unit 202.

It is appreciated that the methods disclosed in FIG. 16 may be implemented in a form of a machine-readable medium embodying a set of instructions that, when executed by a machine, cause the machine to perform any of the operations disclosed herein.

Figure 17:
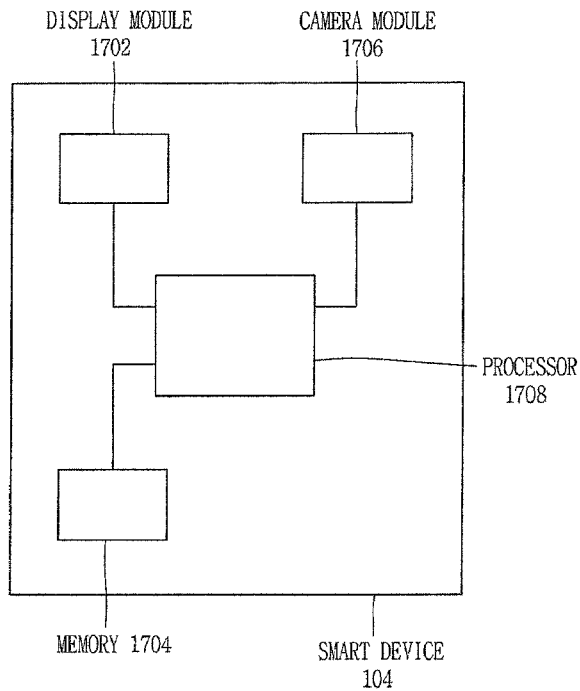
FIG. 17 illustrates an exemplary component view of the smart device in FIGS. 1-16, according to one embodiment of the present invention.

FIG. 17 illustrates an exemplary component view of the smart device 104 in FIGS. 1-16, according to one embodiment of the present invention. In one embodiment, the smart device 104 for analyzing one or more digital images comprises a display module 1702, which is configured to operate the display unit 202, a memory 1704, and a processor 1708 coupled to the display module 1702 and the memory 1704.

The processor 1708 is configured to display, on the display unit 202, a first digital image of a meal and a second digital image of the meal, where the first digital image of the meal is captured before the second digital image of the meal. In addition, the processor 1708 is configured to determine the volume of each food item in the first digital image of the meal and the volume of each food item in the second digital image of the meal by analyzing the first digital image and the second digital image using a digital image processing technique. Further, the processor is configured to generate for displaying on the display unit 202 an amount of intake for the meal based on the difference between the volume of each food item in the first digital image and the volume of each food item in the second digital image.

In one embodiment, the smart device 104 further comprises a digital camera (e.g., of a camera module 1706) configured to capture the first digital image and the second digital image, where the digital camera may be a two-dimensional (2-D) digital camera or a three-dimensional (3-D) digital camera. It is appreciated that although FIG. 17 is described with respect to the embodiments described in FIGS. 1-9, the smart device 104 may also be configured to perform operations implementing the embodiments described in FIGS. 10-16 as well.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and features disclosed herein.

The invention claimed is:

1. A smart device for analyzing food items captured in a digital image for diet watch, the smart device comprising: a display unit; a memory; and a processor coupled to the display unit and the memory and the processor configured to:
   preset a calorie amount as a goal for the diet watch;
   display, on the display unit, a first digital image of a meal and a second digital image of the meal, wherein the first digital image of the meal is captured before the second digital image of the meal;
   determine a volume of each food item in the first digital image of the meal and a volume of the each food item in the second digital image of the meal by analyzing the first digital image and the second digital image using a digital image processing technique; and
   generate for displaying on the display unit an amount of intake for the meal based on a difference between the volume of the each food item in the first digital image and the volume of the each food item in the second digital image,
   wherein the processor is further configured to:
   display, on the display unit, a third digital image of a specific food item, wherein the third digital image of the food item is captured after the second digital image of the meal;
   calculate the remaining calorie amount which can be consumed by a user by subtracting the amount of intake for the meal from the preset calorie amount;
   compare the calculated remaining calorie amount with the total calorie amount of the specific food item; and
   display, on the third digital image, a marking identifying a recommended portion and a caption related to the recommended portion, and
   wherein the recommended portion corresponds to or is less than the remaining calorie amount.

2. The smart device of claim 1, further comprising a digital camera configured to capture the first digital image and the second digital image.

3. The smart device of claim 2, wherein the digital camera is a two-dimensional digital camera or a three-dimensional digital camera.

4. The smart device of claim 1, wherein the amount of intake is in calorie or nutrient weight.

5. The smart device of claim 1, wherein the first digital image of the meal is captured before the meal is eaten and the second digital image of the meal is captured after the meal is eaten.

6. A method of a smart device for analyzing food items captured in a digital image for diet watch, the method comprising:
   presetting a calorie amount as a goal for the diet watch;
   displaying, on a display unit of the smart device, a first digital image of a meal and a second digital image of the meal, wherein the first digital image of the meal is captured before the second digital image of the meal;
   determining a volume of each food item in the first digital image of the meal and a volume of the each food item in the second digital image of the meal by analyzing the first digital image and the second digital image using a digital image processing technique;
   generating, on the display unit, an amount of intake for the meal based on a difference between the volume of the each food item in the first digital image and the volume of the each food item in the second digital image,
   displaying, on the display unit of the smart device, a third digital image of a specific food item, wherein the third digital image of the food item is captured after the second digital image of the meal;
   calculating the remaining calorie amount which can be consumed by a user by subtracting the amount of intake for the meal from the preset calorie amount;
   comparing the calculated remaining calorie amount with the total calorie amount of the specific food item; and
   displaying, on the third digital image, a marking identifying a recommended portion and a caption related to the recommended portion,
   wherein the recommended portion corresponds to or is less than the remaining calorie amount.

7. The method of claim 6, wherein the first digital image of the meal and the second digital image of the meal are received from an external device.

8. The method of claim 6, wherein the first digital image of the meal and the second digital image of the meal are captured using a camera implemented on the smart device.

9. The method of claim 6, wherein the displaying the first digital image further comprises displaying metadata of the each food item on the display unit.

10. The method of claim 9, wherein the metadata comprises identification data of the each food item.

11. The method of claim 9, wherein the metadata comprises an icon for the each food item.

12. The method of claim 9, further comprising associating the each food item on the first digital image with a respective item of the metadata.

13. The method of claim 12, wherein the associating the each food item with the respective item of the metadata is performed when the respective item of the metadata is dragged to a domain of the each food item displayed on the display unit.

14. The method of claim 6, further comprising displaying an image of at least one food item recommended for next meal.

\* \* \* \* \*